US009884314B2

(12) United States Patent
Luo et al.

(10) Patent No.: US 9,884,314 B2
(45) Date of Patent: Feb. 6, 2018

(54) CATALYST COMPOSITION AND REACTIVATION PROCESS USEFUL FOR ALKANE DEHYDROGENATIONS

(71) Applicant: Dow Global Technologies LLC, Midland, MI (US)

(72) Inventors: Lin Luo, Sugar Land, TX (US); Brien A. Stears, League City, TX (US)

(73) Assignee: Dow Global Technologies LLC, Midland, MI (US)

( * ) Notice: Subject to any disclaimer, the term of this patent is extended or adjusted under 35 U.S.C. 154(b) by 128 days.

(21) Appl. No.: 14/420,677

(22) PCT Filed: Jul. 31, 2013

(86) PCT No.: PCT/US2013/052830
§ 371 (c)(1),
(2) Date: Feb. 10, 2015

(87) PCT Pub. No.: WO2014/035590
PCT Pub. Date: Mar. 6, 2014

(65) Prior Publication Data
US 2015/0202601 A1 Jul. 23, 2015

Related U.S. Application Data

(60) Provisional application No. 61/693,892, filed on Aug. 28, 2012.

(51) Int. Cl.
*B01J 21/04* (2006.01)
*B01J 21/08* (2006.01)
(Continued)

(52) U.S. Cl.
CPC ............ *B01J 23/96* (2013.01); *B01J 23/648* (2013.01); *B01J 23/6482* (2013.01);
(Continued)

(58) Field of Classification Search
CPC ... B01J 21/04; B01J 21/08; B01J 21/12; B01J 23/54; B01J 23/56; B01J 23/58;
(Continued)

(56) References Cited

U.S. PATENT DOCUMENTS 2,773,014 A 12/1956 Snuggs et al.
3,880,748 A 4/1975 Sawyer
(Continued)

FOREIGN PATENT DOCUMENTS

DE 2628262 A1 12/1977
EP 0637578 B1 4/1996
(Continued)

OTHER PUBLICATIONS

Chinese Office Action dated Mar. 3, 2016 pertaining to Chinese Application No. 201380056224.8.
(Continued)

*Primary Examiner* — Cam N. Nguyen
(74) *Attorney, Agent, or Firm* — Dinsmore & Shohl LLP

(57) ABSTRACT

A catalyst comprising a Group IIIA metal, a Group VIII noble metal, and an optional promoter metal, on a support selected from silica, alumina, silica-alumina compositions, rare earth modified alumina, and combinations thereof, doped with iron, a Group VIB metal, a Group VB metal, or a combination thereof, offers decreased reactivation time under air soak in comparison with otherwise identical catalysts. Reducing reactivation time may, in turn, reduce costs, both in inventory and capital.

7 Claims, 1 Drawing Sheet

(51) Int. Cl.

| | |
|---|---|
| ***B01J 21/12*** | (2006.01) |
| ***B01J 23/54*** | (2006.01) |
| ***B01J 23/56*** | (2006.01) |
| ***B01J 23/58*** | (2006.01) |
| ***B01J 23/62*** | (2006.01) |
| ***B01J 23/63*** | (2006.01) |
| ***B01J 23/64*** | (2006.01) |
| ***B01J 23/76*** | (2006.01) |
| ***B01J 23/78*** | (2006.01) |
| ***B01J 23/825*** | (2006.01) |
| ***B01J 23/83*** | (2006.01) |
| ***B01J 23/84*** | (2006.01) |
| ***B01J 23/86*** | (2006.01) |
| ***B01J 23/89*** | (2006.01) |
| ***B01J 38/02*** | (2006.01) |
| ***B01J 38/12*** | (2006.01) |
| ***B01J 38/18*** | (2006.01) |
| ***B01J 38/38*** | (2006.01) |
| ***B01J 23/96*** | (2006.01) |
| ***B01J 23/648*** | (2006.01) |
| ***B01J 23/652*** | (2006.01) |
| ***C07C 5/333*** | (2006.01) |

(52) U.S. Cl.

CPC ......... *B01J 23/652* (2013.01); *B01J 23/6522* (2013.01); *B01J 23/8906* (2013.01); *B01J 23/8993* (2013.01); *B01J 38/02* (2013.01); *B01J 38/12* (2013.01); *B01J 38/18* (2013.01); *B01J 38/38* (2013.01); *C07C 5/3337* (2013.01); *C07C 2521/04* (2013.01); *C07C 2521/08* (2013.01); *C07C 2521/12* (2013.01); *C07C 2523/02* (2013.01); *C07C 2523/04* (2013.01); *C07C 2523/08* (2013.01); *C07C 2523/10* (2013.01); *C07C 2523/22* (2013.01); *C07C 2523/26* (2013.01); *C07C 2523/42* (2013.01); *C07C 2523/44* (2013.01); *C07C 2523/46* (2013.01); *C07C 2523/652* (2013.01); *C07C 2523/745* (2013.01); *C07C 2523/89* (2013.01); *Y02P 20/52* (2015.11); *Y02P 20/584* (2015.11)

(58) Field of Classification Search

CPC ........ B01J 23/62; B01J 23/63; B01J 23/6482; B01J 23/6522; B01J 23/76; B01J 23/78; B01J 23/825; B01J 23/83; B01J 23/8472; B01J 23/86; B01J 23/8906; B01J 23/8933; B01J 23/894; B01J 23/8946; B01J 23/896; B01J 23/898; B01J 23/8993; B01J 38/02; B01J 38/12; B01J 38/18; B01J 38/38; C07C 5/3337

See application file for complete search history.

(56) References Cited

U.S. PATENT DOCUMENTS

| | | | | |
|---|---|---|---|---|
| 3,887,495 | A | 6/1975 | Juguin et al. | |
| 3,986,982 | A | 10/1976 | Crowson et al. | |
| 4,215,663 | A | 8/1980 | Gaylord | |
| 4,217,205 | A | 8/1980 | Marcilly et al. | |
| 4,404,123 | A * | 9/1983 | Chu | B01J 23/825 502/174 |
| 4,433,186 | A * | 2/1984 | Chu | B01J 23/825 502/330 |
| 4,476,247 | A * | 10/1984 | Pesa | B01J 27/24 502/200 |
| 4,698,325 | A * | 10/1987 | Andrew | B01J 23/76 423/363 |
| 5,143,886 | A | 9/1992 | Iezzi et al. | |
| 5,258,348 | A * | 11/1993 | Van Buren | B01J 23/00 502/328 |
| 5,354,935 | A * | 10/1994 | Van Buren | B01J 23/00 585/440 |
| 5,457,077 | A | 10/1995 | Williamson et al. | |
| 5,633,421 | A | 5/1997 | Iezzi et al. | |
| 6,362,385 | B1 | 3/2002 | Iezzi et al. | |
| 6,500,781 | B2 * | 12/2002 | Luo | B01J 23/58 502/305 |
| 6,756,339 | B1 * | 6/2004 | Rokicki | B01J 23/894 502/304 |
| 7,235,706 | B2 | 6/2007 | Iezzi et al. | |
| 7,259,286 | B2 * | 8/2007 | Jothimurugesan | B01J 23/78 423/655 |
| 7,452,844 | B2 * | 11/2008 | Hu | C10G 2/333 502/241 |
| 7,473,668 | B2 | 1/2009 | Bartolini et al. | |
| 7,824,455 | B2 * | 11/2010 | Faur-Ghenciu | C01B 3/16 252/373 |
| 8,080,694 | B2 * | 12/2011 | Weiner | B01J 23/626 568/885 |
| 8,288,446 | B2 * | 10/2012 | Mamedov | C01B 3/00 423/651 |
| 8,912,110 | B2 * | 12/2014 | Serban | B01J 23/63 208/134 |
| 9,174,199 | B2 * | 11/2015 | Zhang | B01J 23/62 |
| 9,226,091 | B2 * | 12/2015 | Lyons | H04R 5/04 |
| 9,242,227 | B2 * | 1/2016 | Dakka | B01J 21/08 |

FOREIGN PATENT DOCUMENTS

| | | | |
|---|---|---|---|
| GB | 735145 | A | 8/1955 |
| WO | 2001/56960 | A1 | 8/2001 |
| WO | 2004/052535 | A1 | 6/2004 |
| WO | 2004/110966 | A1 | 12/2004 |
| WO | 2010107591 | A1 | 9/2010 |

OTHER PUBLICATIONS

Chinese Office Action dated Sep. 29, 2016 pertaining to Chinese Application No. 201380056224.8.

International Search Report and Written Opinion for PCT/US2013/052830, dated Oct. 31, 2013, pp. 1-10.

International Preliminary Report on Patentability, Chapter II of the PCT for PCT/US2013/052830, dated Nov. 26, 2014, pp. 1-13.

Office Action dated May 19, 2017 pertaining to Russian Patent Application No. 2015111176.

Chinese Office Action dated Mar. 13, 2017 pertaining to Chinese Application No. 201380056224.8.

* cited by examiner

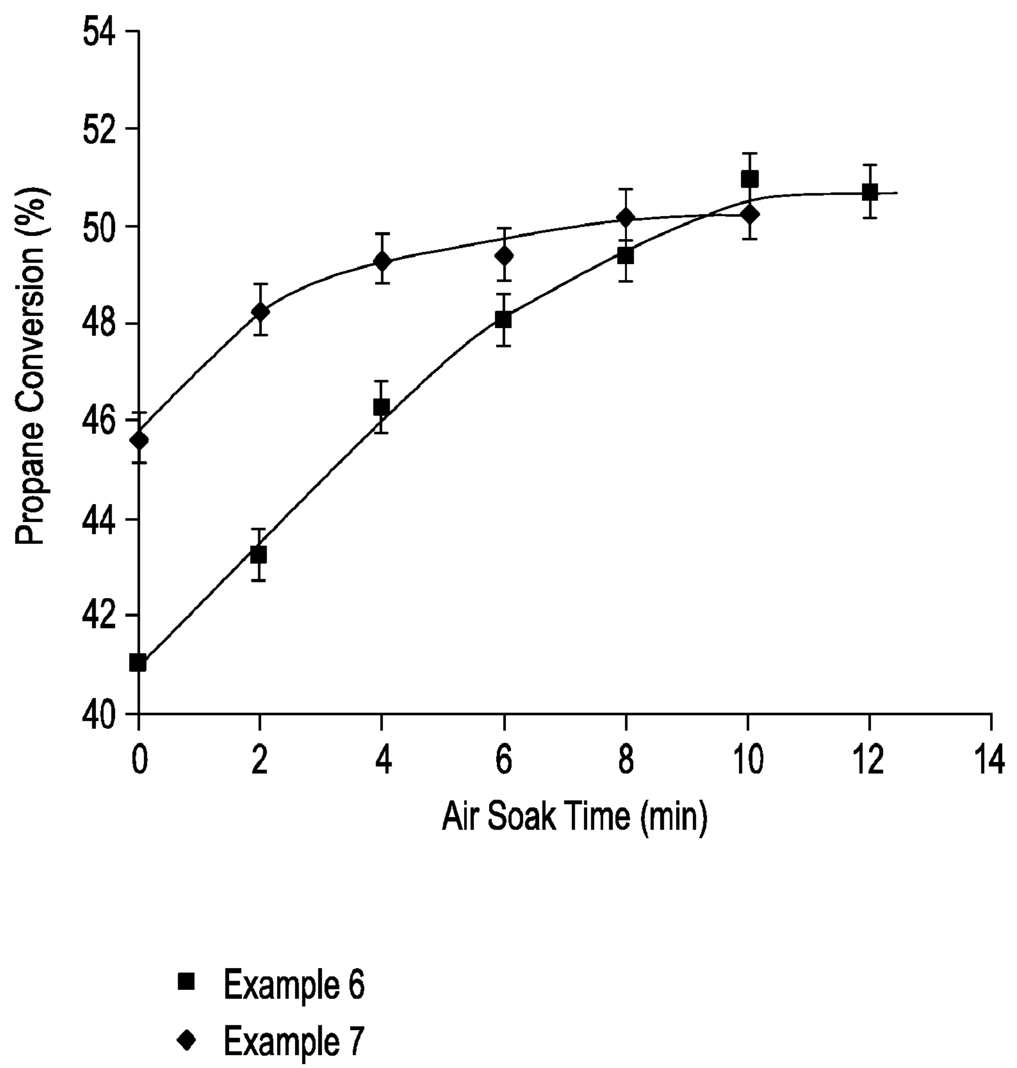
54
52
50
48
46
44
42
40
Propane Conversion (%)
0
2
4
6
8
10
12
14
Air Soak Time (min)
Example 6
Example 7

CATALYST COMPOSITION AND REACTIVATION PROCESS USEFUL FOR ALKANE DEHYDROGENATIONS

REFERENCE TO A RELATED APPLICATION

The present application claims the benefit of U.S. Provisional Application No. 61/693,892, filed on Aug. 28, 2012.

BACKGROUND

1. Field of the Invention

The invention relates to improved catalysts for alkane dehydrogenations and to processes that include reactivating the partially spent catalysts.

2. Background of the Art

Conventional catalyst regeneration processes, that treat catalysts with reduced catalytic activity due, at least in part, to deposition of coke on catalyst surfaces, generally include removal of that coke. This is frequently accomplished by contacting such catalysts with air or another oxygen-containing gas under high temperature conditions. The temperature of such air or other gas may be, for example, greater than or equal to 450 degrees Celsius (° C.) for an ethanol dehydrogenation catalyst, or greater than or equal to 650° C. for a fluid catalyst cracking (FCC) catalyst. In some cases, however, conventional catalyst regeneration processes do not desirably restore catalytic activity of platinum containing supported gallium catalysts or other noble metal based (e.g., platinum-tin containing) dehydrogenation catalysts to a level equaling that of such catalysts when they are fresh. Thus, those who practice alkane dehydrogenation, especially propane dehydrogenation (PDH), understand that, as activity of a catalyst decreases, alkene production also decreases, eventually to a point where process economics dictate replacement of the deactivated catalyst with fresh catalyst. Since commercial viability depends upon optimization of economics, practitioners therefore desire means and/or methods to either more fully restore catalyst activity, or to otherwise delay the need to introduce fresh catalyst in these alkane dehydrogenations.

A typical regeneration of a noble metal based dehydrogenation catalyst involves many steps, frequently including coke combustion, drying and redispersion of the noble metal, and reduction. For example, U.S. Pat. No. 5,457,077 (Williamson, et al.) discloses a process for reconditioning platinum-containing catalyst particles that includes transferring the catalyst particles through both a combustion zone and a reconditioning zone. The reconditioning zone simultaneously effects drying of catalyst particles and redispersion of the platinum with a heated gas stream containing chlorine and oxygen.

U.S. Pat. No. 3,986,982 (Crowson, et al.) discloses chlorine regeneration of zeolite catalysts containing platinum group metals (e.g., platinum (Pt), palladium (Pd), rhodium (Rh), ruthenium (Ru), osmium (Os) and/or iridium (Ir)). This is done by (1) burning off deposits on the catalyst at no more than 500° C.; (2) treating the catalyst with inert gas, which is 0.5 volume percent (vol %) to 20 vol % oxygen and 5 parts by volume per million parts by volume (ppv) to 500 ppv chlorine at a temperature from 400° C. to 550° C.; (3) purging to remove residual oxygen and chlorine; and (4) reducing the catalyst in a stream of hydrogen gas at 200° C. to 600° C.

U.S. Pat. No. 2,773,014 (Snuggs, et al.) discloses hydrocarbon reforming with a platinum catalyst and a regeneration system for the catalyst. Regeneration involves bringing catalyst contained in a fixed reactor bed to an elevated temperature of about 850 degrees Fahrenheit (° F.) (~454° C.) and burning off coke on the catalyst in the presence of a small amount of air. The catalyst is then rejuvenated by exposing it to (1) a circulating gas having an increased oxygen partial pressure of at least 0.4 atmosphere (39.2 kilopascals (kPa)) and (2) an increased bed temperature, e.g., the bed temperature is raised from 950° F. (~510° C.) to 1200° F. (~649° C.). Rejuvenation times depend upon the extent of catalyst deactivation, and range from 5 or 10 minutes, for slightly deactivated catalysts, to as long as 24 hours, for highly deactivated catalysts. Subsequent to rejuvenation the catalyst is purged of oxygen by introducing hydrogen to burn off the oxygen in the system.

British Patent (GB) 735,145 discloses a method for regenerating platinum and/or palladium catalysts that includes treating the catalysts at a temperature from 700° F. (~371° C.) to 1600° F. (~871° C.) with an oxygen-containing gas, where the oxygen partial pressure is from 5 pounds per square inch absolute (psia) (~34.5 kPa) to 200 psia (~1379 kPa). Oxygen associated with the catalyst is then removed by treating with hydrogen gas.

Despite these and other approaches to regeneration and rejuvenation of catalysts, those skilled in the art recognize that any means and/or method that reduces overall time and/or number of steps to accomplish such goal may potentially represent a significant cost savings in a given process. In view of this, it would be desirable in the art to discover means and/or processes to reduce such time or number of steps.

BRIEF DESCRIPTION OF THE DRAWINGS

FIG. 1 is a graph of the percent propane conversion as a function of air for Example 6 and Example 7.

SUMMARY OF THE INVENTION

In one aspect, the invention provides an improvement in an alkane dehydrogenation catalyst comprising a Group IIIA (IUPAC Group 13) metal, a Group VIII (IUPAC Groups 8-10) noble metal, and an optional promoter metal, on a catalyst support selected from silica, alumina, silica-alumina composites, rare earth modified alumina, and combinations thereof, the improvement comprising further including a dopant selected from iron, a Group VIB (IUPAC Group 6) metal, a Group VB (IUPAC Group 5) metal, and combinations thereof.

In another aspect the invention provides a process to dehydrogenate an alkane comprising employing as an alkane dehydrogenation catalyst the previously described improved alkane dehydrogenation catalyst.

In yet another aspect the invention provides a process to at least partially reactivate an at least partially deactivated alkane dehydrogenation catalyst comprising treating this catalyst by exposing it to an oxygen-containing gas at a temperature of at least 660° C., wherein the catalyst comprises a Group IIIA (IUPAC Group 13) metal, a Group VIII (IUPAC Groups 8-10) noble metal, an optional promoter metal, and a dopant selected from iron, a Group VIB (IUPAC Group 6) metal, a Group VB (IUPAC Group 5) metal, and combinations thereof, on a catalyst support selected from the group consisting of silica, alumina, silica-alumina composites, rare earth modified alumina, and combinations thereof; such that the alkane dehydrogenation activity of the at least partially deactivated catalyst is increased to a level such that, upon contact with a selected alkane, it converts the selected alkane to a given percent in a time that is shortened by at least 10 percent in comparison with the time required to increase the alkane dehydrogenation activity, under otherwise identical conditions, of an otherwise identical catalyst to the same level, wherein the otherwise identical catalyst differs only in that it lacks the same amount of the same dopant.

In still another aspect the invention provides an improvement in a process for regenerating an alkane dehydrogenation catalyst, the process including the steps of (a) heating an at least partially deactivated, particulate alkane dehydrogenation catalyst comprising a Group IIIA (IUPAC Group 13) metal, a Group VIII (IUPAC Groups 8-10) noble metal, and an optional promoter metal, on a catalyst support selected from silica, alumina, silica-alumina composites, rare earth modified alumina, and combinations thereof, containing coke thereon, to a temperature of at least 660° C. using heat generated by combusting the coke and from a fuel source other than the coke, this heating yielding a heated, further deactivated catalyst which has an alkane dehydrogenation activity that is less than that of the at least partially deactivated, particulate catalyst; (b) maintaining the heated, further deactivated, particulate alkane dehydrogenation catalyst at a temperature of at least 660° C. while exposing it to a flow of an oxygen-containing gas for a period of time sufficient to increase the activity of the further deactivated, particulate alkane dehydrogenation catalyst and thereby form an at partially reactivated, particulate alkane dehydrogenation catalyst; the at least partially reactivated, particulate alkane dehydrogenation catalyst comprising molecular oxygen trapped within or between the particles thereof and physisorbed oxygen; (c) optionally, maintaining the at least partially reactivated, particulate alkane dehydrogenation catalyst at a temperature of at least 660° C. while exposing it to a flow of stripping gas that is substantially free of both molecular oxygen and combustible fuel for a period of time such that at least a portion of both the molecular oxygen trapped within or between catalyst particles, and of the physisorbed oxygen that is desorbable at that temperature during that period of time, are removed from the at least partially reactivated, particulate alkane dehydrogenation catalyst, thereby forming a rejuvenated, particulate alkane dehydrogenation catalyst; and (d) transporting the rejuvenated, particulate alkane dehydrogenation catalyst to the reactor by means of at least a motive force; the improvement comprising employing as a constituent of the particulate alkane dehydrogenation catalyst an effective amount of a dopant selected from iron, a Group VIB (IUPAC Group 6) metal, a Group VB (IUPAC Group 7) metal, and combinations thereof, such that the time required in step (b) to increase the activity level of the further deactivated, particulate alkane dehydrogenation catalyst, such that, upon contact with a selected alkane, it converts the selected alkane to a given percent, in a time that is shortened by at least 10 percent in comparison with the time required to increase an otherwise identical further deactivated, particulate alkane dehydrogenation catalyst to the same activity level under identical conditions, wherein the otherwise identical further deactivated, particulate alkane dehydrogenation catalyst differs only in that it lacks the effective amount of the dopant.

In particular embodiments the dopant is present in an effective amount which, where the dopant is iron, ranges from greater than 100 parts by weight to 2100 parts by weight; and where the dopant is a Group VIB (IUPAC Group 6) metal, such as chromium, or a Group VB (IUPAC Group 5) metal, such as vanadium, ranges from 100 parts by weight to 800 parts by weight; in each case per million parts by weight of alkane dehydrogenation catalyst.

It is noted that Group IIIA, Group VIII, Group VB and Group VIB, as used hereinabove, refer to designations in *Periodic Table of the Elements* (Chemical Abstract Service, CAS, version), while IUPAC Group 13, IUPAC Groups 8-10, IUPAC Group 6, and IUPAC Group 5 refer to the *Periodic Table of the Elements* (2007 version) promulgated by the International Union of Pure and Applied Chemistry (IUPAC).

Detailed Description of The Embodiments

The invention offers a significant shortening in the "air soak time," i.e., oxygen treatment time, needed to at least partially reactivate a defined, at least partially deactivated alkane dehydrogenation catalyst, which comprises employing as the catalyst one containing, in particular, one or two particular dopants, preferably in given effective amounts. Use of the inventive catalyst, in certain alkane dehydrogenation processes, may, therefore, reduce overall dehydrogenation process costs to a manufacturer. As the term is used herein, and as will be seen in greater detail hereinbelow, the term "reactivation" refers to an increase in the activity of a catalyst, spent by use in a given reaction application, to enable reuse in the same reaction application, for example, in dehydrogenation, and comprehends a single step, alternatively referred to herein as "air soak." This is contrasted with "regeneration," which is a more generalized term for a restoration of usability of a catalyst, and may comprehend a multi-step procedure.

In general a circulating fluidized bed based process for dehydrogenating an alkane may be described as including placing an alkane in operative contact, in a reactor, with the inventive supported catalyst, which has preferably been heated. In such a process the catalyst employed herein comprises as constituents a Group IIIA (IUPAC Group 13) metal, which is desirably selected from gallium (Ga), indium (In), thallium (Tl), and combinations thereof; a Group VIII (IUPAC Groups 8-10) noble metal, which is desirably selected from platinum (Pt), palladium (Pd), rhodium (Rh), iridium (Ir), ruthenium (Ru), osmium (Os), and combinations thereof; optionally, a promoter metal, which is preferably an alkali or alkaline earth metal desirably selected from sodium (Na), potassium (K), rubidium (Rb), cesium (Cs), magnesium (Mg), calcium (Ca), strontium (Sr), barium (Ba), and combinations thereof; and a dopant, as further described hereinbelow.

In general it is preferred that the amount of the Group IIIA (IUPAC Group 13) metal, and in particular embodiments Ga, ranges from 0.25 percent by weight (wt %) to 5 wt %, with a very small amount of the Group VIII (IUPAC Groups 8-10) noble metal, and in particular embodiments Pt, included, ranging from 5 parts by weight to 500 parts by weight, each percent being by weight based upon total alkane dehydrogenation catalyst and each part by weight being based upon one million parts by weight of alkane dehydrogenation catalyst. Furthermore, it is desirable that the promoter metal, for example, potassium, is employed in an amount ranging from 0 wt % to 2.0 wt %, based on the weight of the alkane dehydrogenation catalyst.

The dopant, which may be selected from iron; a Group VIB (IUPAC Group 6) metal, including but not limited to chromium; a Group VB (IUPAC Group 5) metal, including but not limited to vanadium; and combinations thereof; is a further and important catalyst constituent. In the present invention such is desirably included in any effective amount, which depends upon identification of the dopant but may also depend on other and/or additional parameters of the reaction. The effective amount may therefore be considered to be the doping amount, i.e., the ranging amount of a given dopant at which the advantage of the invention, i.e., the described shortening of the time to accomplish a given level of reactivation of the catalyst is accomplished, in view of the totality of the reaction parameters. Where the dopant is iron, such is desirably in an amount ranging from 100 parts by weight to 2100 parts by weight. Where it is chromium, vanadium, or another of the Group VIB (IUPAC Group 6) or Group VB (IUPAC Group 5) metals, such is desirably in an amount ranging from 100 parts by weight to 800 parts by weight. In each case, calculation of parts by weight is per million parts by weight of the catalyst. These preferred amounts apply without alteration regardless of whether either dopant is used alone or in combination.

Finally, the catalyst is desirably supported on a medium selected from silica, alumina, silica-alumina composites, rare earth modified alumina, and combinations thereof. These supports make the catalyst particularly effective for use in, for example, fixed, fluidized, or moving bed processes.

The above-described alkane dehydrogenation catalyst may be suitably used to carry out an alkane dehydrogenation process, with such process desirably occurring under conditions that are, for reasons of convenience, economics, and avoidance of degradation and undesirable side reactions, as mild as possible. Following completion of dehydrogenation to a desirable extent, the at least partially deactivated catalyst may then be removed from the reactor; treated to at least partially reactivate it; and transported back to the reactor.

In one non-limiting embodiment it may be desirable to carry out catalyst regeneration by means of the steps of:

(a) heating the particulate alkane dehydrogenation catalyst defined hereinabove [containing the effective amount of the dopant], which has been at least partially deactivated and contains coke thereon, to a temperature of at least 660° C. using heat generated by combusting the coke and from a fuel source other than the coke, this heating yielding a heated, further deactivated catalyst which has an alkane dehydrogenation activity that is less than that of the at least partially deactivated, particulate catalyst;

(b) maintaining the heated, further deactivated, particulate alkane dehydrogenation catalyst at a temperature of at least 660° C. while exposing it to a flow of an oxygen-containing gas for a period of time sufficient to increase the activity level of the further deactivated, particulate alkane dehydrogenation catalyst and thereby form an at partially reactivated, particulate alkane dehydrogenation catalyst; wherein the time required to increase the activity level of the further deactivated, particulate alkane dehydrogenation catalyst, such that it is enabled to dehydrogenate a given alkane to a given percent, is reduced by at least 10 percent in comparison with the time required to increase an otherwise identical further deactivated, particulate alkane dehydrogenation catalyst to the same activity level under identical conditions, wherein the otherwise identical further deactivated, particulate alkane dehydrogenation catalyst differs only in that it lacks the dopant;

the at least partially reactivated, particulate alkane dehydrogenation catalyst comprising molecular oxygen trapped within or between the particles thereof and physisorbed oxygen;

(c) optionally, maintaining the at least partially reactivated, particulate alkane dehydrogenation catalyst at a temperature of at least 660° C. while exposing it to a flow of stripping gas that is substantially free of both molecular oxygen and combustible fuel for a period of time such that at least a portion of both the molecular oxygen trapped within or between catalyst particles, and of the physisorbed oxygen that is desorbable at that temperature during that period of time, are removed from the at least partially reactivated, particulate alkane dehydrogenation catalyst, thereby forming a rejuvenated, particulate alkane dehydrogenation catalyst; and (d) transporting the rejuvenated, particulate alkane dehydrogenation catalyst to the reactor by means of a motive force, such as an inert transport gas, gravity, or a combination thereof.

"At least partially deactivated dehydrogenation catalyst" means a catalyst as provided by the invention with a dehydrogenation activity that is greater than 70%, but less than 95%, of the dehydrogenation activity of the same catalyst prior to its use in the given desired alkane dehydrogenation, such as, in non-limiting example, propane dehydrogenation (PDH), wherein propane is converted to form propylene and hydrogen ($H_2$).

"Further deactivated alkane dehydrogenation catalyst" refers to a catalyst as provided by the invention that, subsequent to heating step (a), has a dehydrogenation activity at least 5% lower than the activity of the at least partially deactivated alkane dehydrogenation catalyst prior to step (a). By way of example, if the at least partially deactivated alkane dehydrogenation catalyst has an alkane dehydrogenation activity of 90%, the further deactivated alkane dehydrogenation catalyst has an alkane dehydrogenation activity of 85% or less.

While particularly suitable for dehydrogenating propane, the inventive process employing the inventive catalysts may be used for dehydrogenating other alkanes, including ethane, butane, and pentane to their respective alkenes (e.g., to ethylene, when the alkane being dehydrogenated is ethane). The resulting alkene (e.g., propylene, ethylene or butylene) has utility as, for example, a monomer in polymerization processes to produce products including, but not limited to, polyethylene, polypropylene, and ethylene-propylene copolymers.

The period of time for reactivation step (b) is desirably from 2 minutes (min) to 20 min, and preferably from 4 min to 14 min. This period of time has an inverse relationship to temperature for at least step (b) and, in particular embodiments, for both steps (a) and (b). In other words, to reach a desired level of reactivation for dehydrogenating alkane, as temperature increases (e.g., as it nears 850° C.), less time is needed to accomplish step (b) than would be required for the same reactivation step at lower temperature (e.g., closer to 660° C.). Similarly, increasing the temperature may also hasten the further deactivation of step (a). The desired final level of catalyst activity resulting from completion of step (b) is a matter of choice, but preferably approaches or is equal to that of fresh (previously unused) heated alkane dehydrogenation catalyst prior to the initial operative contact with an alkane in the reactor.

The temperatures for steps (a), (b), and (c) are preferably, and independently, at least 660° C. A practical upper limit is 850° C., which helps to avoid challenges such as undesirable side reactions or damage to apparatus components used in conjunction with the process. The temperatures for each of steps (a), (b) and (c) are preferably, and independently, from 660° C. to 780° C., still more preferably from 700° C. to 780° C., and yet still more preferably from 700° C. to 750° C. More specifically, for step (b), a temperature of at least 660° C. has been found to be particularly efficacious, more particularly a temperature ranging from 660° C. to 850° C., and preferably from 700° C. to 780° C. Pressure may desirably range from 68.9 kilopascals (kPa) to 413.7 kPa, and preferably from 172.4 kPa to 275.8 kPa.

It is noted that step (c) does not operate to further increase catalyst activity, but rather removes oxygen to improve catalyst selectivity. This step preferably comprises maintaining the heated catalyst at a temperature within the specified temperature range and exposing the heated catalyst to a flow of a non-oxygen gas. The gas is preferably an inert gas such as nitrogen ($N_2$), in sufficient amount to remove at least a portion of, more preferably substantially all of, any residual combustion byproducts and residual oxygen that are present on the heated catalyst following the reactivation. The non-oxygen gas is defined as containing no more than 0.5 vol %, preferably no more than 0.05 vol % of oxygen. It may also contain, in less preferred embodiments, very small amounts of carbon oxides such as carbon dioxide (no more than 1 vol %), carbon monoxide (no more than 0.1 vol %) and/or water (no more than 2 vol %). However, those skilled in the art will understand that minimizing these potential oxygen sources will improve the ultimate selectivity of the catalyst.

In process embodiments where a process including at least a step (a), step (b), and step (c) has been carried out, the rejuvenated dehydrogenation catalyst preferably has substantially the same or similar activity for dehydrogenating an alkane, such as propane, as the at least partially reactivated dehydrogenation catalyst, but a lower activity for forming carbon oxides than the at least partially reactivated dehydrogenation catalyst, due to the reduced amount of trapped or physisorbed oxygen in the rejuvenated catalyst. Such catalyst is also substantially free of coke, which means that it has a coke content of less than 0.05 percent by weight (wt %), based upon total catalyst weight. In particular embodiments, the rejuvenated dehydrogenation catalyst has a residual oxygen content of less than 0. 1 wt %, based upon total catalyst weight. It may also desirably exhibit a combustion product content of less than 1 wt % carbon dioxide and less than 0.2 wt % water, in each case based upon catalyst weight; and desirably less than 100 parts by weight per million parts by weight of catalyst (ppmw) of carbon monoxide (CO).

EXAMPLES

Example 1

Comparative

A Base Catalyst is synthesized by the conventional incipient wetness method. An amount, 120 grams (g) of SIRALOX™ 1.5/70 support (alumina doped with 1.5 wt % silica, commercially available from Sasol) is pre-dried at 177° C. for 1 hour (h) and then cooled down to ambient temperature in a desiccator. Amounts of constituents including 0.016 g of tetraamine platinum nitrate ($Pt(NH_3)_4(NO_3)_2$), 0.664 g of potassium nitrate ($KNO_3$), and 8.56 g of gallium nitrate hexahydrate ($Ga(NO_3)_3.6H_2O$) are dissolved in 24.0 milliliters (mL) of deionized (DI) water. The dissolved metal precursors are added dropwise to 100 g of the pre-dried SIRALOX™ 1.5/70 support. The SIRALOX™ 1.5/70 support is stirred constantly during the metal precursor addition. The metal impregnated material is placed in a fume hood overnight, followed by drying at 120° C. for 4 h and calcination at 750° C. for 4 h. The resulting Base Catalyst has a Pt content of 80 parts by weight per million parts by weight (ppm) of Base Catalyst, a K content of 0.25 wt % and a Ga content of 1.6 wt %, each wt % being based upon Base Catalyst weight.

Examples 2-4

Chromium-promoted inventive catalysts (containing 100, 250, 500 and 1000 ppm chromium, respectively, Example 2, except that 100 ppm and 1000 ppm are outside of effective amount range); iron-promoted inventive catalysts (containing 500 and 1000 ppm iron, respectively, Example 3); and a chromium/iron-promoted inventive catalyst (containing 500 ppm chromium and 500 ppm iron, Example 4); are then prepared by loading the Base Catalyst with iron and/or chromium as appropriate, using the incipient wetness method described above. $Fe(NO_3)_3.9H_2O$ and $Cr(NO_3)_3.9H_2O$ are the metal precursors used. The amount of the metal precursors is calculated based on the targeted iron and chromium concentration on the catalysts. The metal precursor(s) is/are dissolved in DI water prior to loading onto the Base Catalyst. The obtained material is then dried at 120° C. for 4 h, followed by calcination at 600° C. for 4 h in a box furnace.

Example 5

Comparative

The comparative catalyst ("Base Catalyst") prepared in Comparative Example 1 and the inventive catalysts prepared in Examples 2-4 are evaluated according to the following protocol.

First, 0.5 g of each catalyst is premixed with 1.0 g silicon carbide (SiC). Each catalyst is then subjected to a number of dehydrogenation reaction/catalyst reactivation/catalyst rejuvenation cycles as detailed below. In the reaction step, PDH is effected for 60 seconds (sec) at 620° C. using a feed stream that contains 95 mole percent (mol %) propane and 5 mol % nitrogen ($N_2$), each mol % being based upon total moles in the feed stream and the $N_2$ serving as an internal standard (ISD). The propane weight hourly space velocity (WHSV) is 8 reciprocal hours ($hr^{-1}$). Data is then collected for propane conversion and propylene selectivity at approximately 12 sec catalyst on stream.

After 60 sec, the reactor temperature is ramped to 730° C. at a rate of 20° C. per minute in the presence of a gas stream (specified below) that flows through the reactor at a rate of 120 standard cubic centimeters per minute (sccm). This is not step (a), but is, rather, a laboratory scale step used to increase the temperature from the dehydrogenation reaction temperature to regeneration temperature. In commercial operation, a much shorter stripping step would be applied.

The catalyst then begins regeneration with a simulated step (a), wherein it is interacted with a simulated combustion by-products stream under a maintained temperature of 730° C. for 3 min. The simulated combustion by-products stream has a flow rate of 150 sccm and a composition of 4 mol % $O_2$, 8 mol % $CO_2$, 16 mol % $H_2O$, with balanced helium (He).

An "air soak" with 100% air and a flow rate of 150 sccm is then carried out as reactivation step (b). The time for the air soak is varied to reach according to targeted PDH conversions of 48%, 49%, 50%, and 51%, respectively. Table 1 shows the time required, in minutes, to at least partially reactivate the catalyst to enable each given conversion level.

Following the reactivation step (b) and before starting another PDH reaction cycle, the reactor is cooled to the reaction temperature (620° C.) and the temperature of the system is stabilized over a period of 20 min under flowing He (flow rate of 120 sccm) to effect stripping of labile oxygen from the catalyst (step (c)) and also allow the temperature of the catalyst bed to be stable before the next reaction regeneration cycle.

TABLE 1

Time required, in minutes, to form reactivated (step (b)) catalyst to given conversion levels.

| | Example 1 | Example 2 | | | | Example 3 | | Example 4 |
|---|---|---|---|---|---|---|---|---|
| Conversion | (Comparative) | 100 ppm* Cr | 250 ppm Cr | 500 ppm Cr | 1000 ppm** Cr | 500 ppm Fe | 1000 ppm Fe | 500 ppm Cr, 500 ppm Fe |
| 50% | 8.4 | 8.8 | 6.4 | 5.7 | — | 7.0 | 5.9 | 7.2 |
| 52% | 15.0 | 14.3 | 10.9 | 10.2 | >15.0 | 11.8 | 9.7 | 11.7 |

— denotes no data
*denotes amount lower than effective amount
**denotes amount higher than effective amount
>denotes greater than

Examples 6-7

Two inventive catalysts are prepared using the method of Examples 2-4, but having the constituency shown in Table 2 hereinbelow, to compare the effect of differing amounts of dopants.

TABLE 2

Constituency of catalysts.

| Example | Pt, ppm | Cr, ppm | Fe, ppm | K, ppm | Ga, wt % |
|---|---|---|---|---|---|
| 6 | 72 | 110 | 530 | 2200 | 1.6 |
| 7 | 78 | 560 | 2020 | 2200 | 1.50 |

These catalysts are then tested, according to the method of Example 5 (Comparative), to determine the amount of time required for each to be reactivated to enable a given conversion level. Results of this testing are shown in Table 3 hereinbelow.

TABLE 3

Time required to reactivate catalyst to given conversion levels.

| Conversion | Example 6, min | Example 7, min |
|---|---|---|
| 50% | 8.4 | 8.1 |
| 49% | 6.9 | 3.3 |
| 48% | 5.4 | 1.8 |

Example 8

Comparative

The catalysts prepared in Examples 6-7 are compared using FIG. 1 for more convenient visualization. FIG. 1 shows that Example 7 requires less reactivation (i.e., "air soak") time than does Example 6, despite equivalent Pt loading, due to Example 7's higher iron and chromium content. For example, Example 7 achieves a propane percent conversion of about 48% at 4 minutes air soak, while Example 6 does not reach the same percent conversion until about 8 minutes. However, at propane conversions greater than about 50 percent, the lower iron and chromium contents of Example 6 appear to approximately equal, with the small difference observed being within instrument error expectations. Both catalysts are considered to be inventive.

We claim:

1. An alkane dehydrogenation catalyst composition comprising a Group IIIA metal selected from gallium, indium, thallium and combinations thereof, wherein the Group IIIA metal ranges from 0.25 percent by weight to 5 percent by weight;

a Group VIII noble metal selected from platinum, palladium, rhodium, iridium, ruthenium, osmium, and combinations thereof, wherein the Group VIII noble metal ranges from 5 parts by weight to 500 parts by weight;

at least one dopant selected from iron, chromium, vanadium, and combinations thereof, wherein:

when iron is present, iron ranges from 100 parts by weight to 2100 parts per weight;

when chromium is present, chromium ranges from 100 parts by weight to 800 parts by weight; and when vanadium is present, vanadium ranges from 100 parts by weight to 800 parts by weight;

and an optional promoter metal selected from sodium, potassium, rubidium, cesium, magnesium, calcium, strontium, barium and combinations thereof, wherein the optional promoter metal ranges from 0 percent by weight to 2.0 percent by weight;

wherein each percent by weight based upon weight of the total alkane dehydrogenation catalyst, and each part by weight based upon one million parts by weight of the total alkane dehydrogenation catalyst;

on a catalyst support selected from silica, alumina, silica-alumina composites, rare earth modified alumina, and combinations thereof.

2. The catalyst composition of claim 1 wherein at least one selection is made from: the alkane is propane, the Group VIII noble metal is platinum, the Group IIIA metal is gallium, the optional promoter metal is potassium, and combinations thereof.

3. A process to dehydrogenate an alkane comprising employing as an alkane dehydrogenation catalyst the catalyst composition of claim 1.

4. A process to at least partially reactivate the alkane dehydrogenation catalyst of claim 1, which has been at least partially deactivated comprising treating the at least partially deactivated alkane dehydrogenation catalyst by exposing it to an oxygen-containing gas at a temperature of at least 660° C., such that the alkane dehydrogenation activity of the at least partially deactivated alkane dehydrogenation catalyst is increased to a level such that, upon contact with a selected alkane, it converts the selected alkane to a given percent in a time that is shortened by at least 10 percent in comparison with the time required to increase the alkane dehydrogenation activity, under otherwise identical conditions, of an otherwise identical alkane dehydrogenation catalyst to the same level, wherein the otherwise identical alkane dehydrogenation catalyst differs only in that it lacks the same amount of the same dopant.

5. The process of claim 4 wherein at least one selection is made from: the alkane is propane; the Group IIIA metal is gallium; the Group VIII noble metal is platinum; the optional promoter metal is potassium; and combinations thereof.

6. The process of claim 4 for regenerating an alkane dehydrogenation catalyst, the process including the steps of (a) heating the at least partially deactivated, particulate alkane dehydrogenation catalyst containing coke thereon, to a temperature of at least 660° C. using heat generated by combusting the coke and from a fuel source other than the coke, this heating yielding a heated, further deactivated catalyst which has an alkane dehydrogenation activity that is less than that of the at least partially deactivated, particulate catalyst;

(b) maintaining the heated, further deactivated, particulate alkane dehydrogenation catalyst at a temperature of at least 660° C. while exposing it to a flow of an oxygen-containing gas for a period of time sufficient to increase the activity of the further deactivated, particulate alkane dehydrogenation catalyst and thereby form an at partially reactivated, particulate alkane dehydrogenation catalyst; the at least partially reactivated, particulate alkane dehydrogenation catalyst comprising molecular oxygen trapped within or between the particles thereof and physisorbed oxygen;

(c) optionally, maintaining the at least partially reactivated, particulate alkane dehydrogenation catalyst at a temperature of at least 660° C. while exposing it to a flow of stripping gas that is substantially free of both molecular oxygen and combustible fuel for a period of time such that at least a portion of both the molecular oxygen trapped within or between catalyst particles, and of the physisorbed oxygen that is desorbable at that temperature during that period of time, are removed from the at least partially reactivated, particulate alkane dehydrogenation catalyst, thereby forming a rejuvenated, particulate alkane dehydrogenation catalyst; and (d) transporting the rejuvenated, particulate alkane dehydrogenation catalyst to the reactor by means of at least a motive force;

provided that the time required in step (b) to increase the activity level of the further deactivated, particulate alkane dehydrogenation catalyst, such that, upon contact with a selected alkane, it converts the selected alkane to a given percent, in a time that is shortened by at least 10 percent in comparison with the time required to increase an otherwise identical further deactivated, particulate alkane dehydrogenation catalyst to the same activity level under identical conditions, wherein the otherwise identical further deactivated, particulate alkane dehydrogenation catalyst differs only in that it lacks the effective amount of the dopant.

7. The process of claim 6 wherein at least one selection is made from: the alkane is propane; the Group IIIA metal is gallium; the Group VIII noble metal is platinum; the optional promoter metal is potassium; the Group VIB metal is chromium; the Group VB metal is vanadium; and combinations thereof.

* * * * *